(12) United States Patent
Bonniaud et al.

(10) Patent No.: US 9,326,993 B2
(45) Date of Patent: May 3, 2016

(54) TREATMENT OF PULMONARY AND PLEURAL FIBROSIS USING HSP27 INHIBITORS

(71) Applicant: ONCOGENEX TECHNOLOGIES INC., Vancouver (CA)

(72) Inventors: Philippe Bonniaud, Dijon (FR); Carmen Garrido, Talant (FR); Guillaume Wettstein, Dijon (FR)

(73) Assignee: ONCOGENEX TECHNOLOGIES INC., Vancouver (CA)

( * ) Notice: Subject to any disclaimer, the term of this patent is extended or adjusted under 35 U.S.C. 154(b) by 0 days.

(21) Appl. No.: 14/573,145

(22) Filed: Dec. 17, 2014

(65) Prior Publication Data
US 2015/0126584 A1   May 7, 2015

Related U.S. Application Data

(63) Continuation of application No. 13/470,780, filed on May 14, 2012, now Pat. No. 8,987,223.

(60) Provisional application No. 61/485,501, filed on May 12, 2011.

(51) Int. Cl.
| | | |
|---|---|---|
| *C12N 15/11* | (2006.01) | |
| *C12N 15/113* | (2010.01) | |
| *C12N 15/115* | (2010.01) | |
| *A61K 31/713* | (2006.01) | |
| *A61K 31/74* | (2006.01) | |
| *A61K 38/21* | (2006.01) | |
| *A61K 39/395* | (2006.01) | |
| *A61K 31/337* | (2006.01) | |
| *A61K 31/353* | (2006.01) | |
| *A61K 31/4375* | (2006.01) | |

(52) U.S. Cl.
CPC ............. *A61K 31/713* (2013.01); *A61K 31/337* (2013.01); *A61K 31/353* (2013.01); *A61K 31/4375* (2013.01)

(58) Field of Classification Search
None
See application file for complete search history.

(56) References Cited

U.S. PATENT DOCUMENTS

| 6,887,853 B2 | 5/2005 | Strehlow |
|---|---|---|
| 7,763,256 B2 | 7/2010 | Gomer et al. |
| 2001/0049357 A1 | 12/2001 | De et al. |
| 2004/0127441 A1 | 7/2004 | Gleave et al. |
| 2006/0003954 A1 | 1/2006 | Nath et al. |
| 2007/0003555 A1 | 1/2007 | LeClair |
| 2009/0196927 A1 | 8/2009 | Panitch et al. |
| 2009/0264502 A1 | 10/2009 | Bennett et al. |
| 2010/0324115 A1 | 12/2010 | Rodriguez-Lafrasse et al. |

FOREIGN PATENT DOCUMENTS

| EP | 0813872 A1 | 12/1997 |
|---|---|---|
| JP | 10036261 A | 2/1998 |
| JP | 10036267 A | 2/1998 |
| JP | 10045572 A | 2/1998 |
| JP | 10045574 A | 2/1998 |

OTHER PUBLICATIONS

Database NCBI GenBank Ascession No. AB020027.1, *Homo sapiens* HSP27 mRNA, complete cds, Apr. 20, 2002.
Database NCBI GenBank Ascession No. X54079.1, Human mRNA for heat shock protein HSP27, Oct. 7, 2008.
Database NCBI Reference Sequence: NP_001020740.1, heat shock protein beta-1 [Bos taurus], Jun. 27, 2010.
Database NCBI Reference Sequence: NP_001003295.1, heat shock protein beta-1 [Canis lupus familiaris], Jun. 5, 2011.
Database NCBI Reference Sequence: NP_038588.2, heat shock protein beta-1 [Mus musculus], May 14, 2011.
Database NCBI Reference Sequence: NM_006308.2, *Homo sapiens* heat shock 27kDa protein 3 (HSPB3), mRNA, Mar. 10, 2011.
Database NCBI Reference Sequence: NM_001541.3, *Homo sapiens* heat shock 27kDa protein 2 (HSPB2), mRNA. Mar. 13, 2011.
Database NCBI Reference Sequence: NM_001540.3, *Homo sapiens* heat shock 27kDa protein 1 (HSPB1), mRNA, May 22, 2011.
Foucher et al., www.pneumotox.com, The drug-induced lung disease. [Website] Jul. 2011, 2002.
Andrieu, C. et al., Heat shock protein 27 confers resistance to androgen ablation and chemotherapy in prostate cancer cells through eIF4E, Oncogene, 2010, pp. 1883-1896, vol. 29.
American Thoracic Society, Idiopathic Pulmonary Fibrosis: Diagnosis and Treatment; International Consensus Statement, Am J Respir Crit Care Med, 2000, pp. 646-664, vol. 161.
Bruey, JM. et al., Hsp27 negatively regulates cell death by interactin with cytochrome c, Nat Cell Biol, 2000, pp. 645-652, vol. 2, No. 9.
Horman, S. et al., Anti-sense inhibition of small-heat-shock-protein (HSP27) expression in MCF-7 mammary-carcinoma cells induces their spontaneous acquisition of a secretory phenotype, Int J Cancer, 1999, pp. 574-582, vol. 82(4).
De Thonel A. et al., HSP27 controls GATA-1 protein level during erythroid cell differentiation, Blood; 2010, pp. 85-96, vol. 116; Online http://bloodjournal.hematologylibrary.org/content/116/1/85.long, pp. 1-15, Publisher: The American Society of Hematology.
Decologne, N. et al., Bieomycin induces pleural and subpleural fibrosis in the presence of carbon particies, Eur Respir J, 2010, pp. 176-185, vol. 35.
Decologne, N et al., TGF-B1 Induces Progressive Pleural Scarring and Subpleural Fibrosis, The Journal of Immunology, 2007, pp. 6043-6051, vol. 179.
Crosby, J. R. et al., Inhaled CD86 Antisense Oligonucleotide Suppresses Pulmonary Inflammation and Airway Hyper-Responsiveness in Allergic Mice, The Journal of Pharmacology and Experimental Therapeutics; 2007, pp. 938-946, vol. 321, No. 3.

(Continued)

*Primary Examiner* — Christine J Saoud
*Assistant Examiner* — Jegatheesan Seharaseyon
(74) *Attorney, Agent, or Firm* — Larson & Anderson, LLC

(57) ABSTRACT

Reduction of HSP27 expression is in beneficial in the treatment of pleural and pulmonary fibrosis and in particular subpleural fibrosis and IPF. Pharmaceutical compositions for this purpose contain an inhibitor of HSP27 and a pharmaceutically acceptable carrier.

8 Claims, 9 Drawing Sheets

(56) References Cited

OTHER PUBLICATIONS

Cool, C. D. et al., Fibroblast Foci Are Not Discrete Sites of Lung injury or Repair: The Fibroblast Reticulum, Am J Respir Crit Care Med, 2006, pp. 654-658, vol. 174.

Chilosi, M et al., Migratory marker expression in fibroblast foci of idiopathic pulmonary fibrosis, Respiratory Research, 2006, 7:95, http://respiratory-research.com/content/7/1/95, pp. 1-10

Chauhan, D. et al., Blockade of Hsp27 Overcomes Bortezomib/Proteasonie Inhibitor PS-34 Resistance in Lymphoma Cells, Cancer Research, 2003, pp. 6174-6177, vol. 63.

Bonniaud, P. et al., Progressive Transforming Growth Factor B1-induced Lung Fibrosis Is Blocked by an Orally Active ALK5 Kinase Inhibitor, Am J Respir Crit Care Med, 2005, pp. 889-898, vol. 171.

Bett: A. J. et al., An efficient and flexible system for construction of adenovirus vectors with insertions or deletions in early regions 1 and 3, Proc. Natl. Acad. Sci USA, 1994, pp. 8802-8806, vol. 91.

Matsui, Y. et al. Intravesical combination treatment with antisense oligonucleotides targeting heat shock protein-27 and HTI-286 as a novel strategy for high-grade bladder cancer, Mol Cancer Ther, 2009, pp. 2402-2411, vol. 8.

Korfel, M. et al., Comparative Proteomic Analysis of Lung Tissue from Patients with Idiopathic Pulmonary Fibrosis (IPF) and Lung Transplant Donor Lungs, Journal of Proteome Research, 2011, e Pub ahead of print, pp. 1-73.

Kasai, H. et al., TGF-B1 induces human alveolar epithelial to mesenchymal cell transition (EMT), Respiratory Research, 2005, 6:56, Online publication: http://respiratory-research.com/content/6/1/56, pp. 1-15.

Wilson, MS et al., Pulmonary fibrosis: pathogenesis, etiology and regulation, Mucosal Immunol, 2009, pp. 103-121, vol. 2, No. 2.

Brunet Simioni, M. et al., Heat shock protein 27 is involved in SUMO-2/3 modification of heat shock factor 1 and thereby maculates the transcription factor activity, Oncogene, 2009, pp. 3332-3344, vol. 28(37) Epub Jul. 13, 2009.

Tezel, G. et al., The Mechanisms of hsp27 Antibody-Mediated Apoptosis in Retinal Neuronal Cells, The Journal of Neuroscience, 2000, pp. 3552-3562, vol. 10, No. 10.

Sime P. J. et al., Adenovector-mediated Gene Transfer of Active Transforming Growth Factor-B1 Induces Prolonged Severe Fibrosis in Rat Lung, The Journal of Clinical Investigation, 1997, pp. 768-776, vol. 100 No. 4.

Shin, K D et al., Blocking Tumor Cell Migration and Invasion with Biphenyl Isoxazole Derivative KRIBB3, a Synthetic Molecule That Inhibits Hsp27 Phosphoryiation, The Journal of Biological Chemistry, 2005 pp. 41439-41448, vol. 280, No. 50, Publisher. The American Society for Biochemistry and Molecular Biology, Inc., Printed in the USA.

Shashidharamurthy, R. et al., Mechanism of Chaperone Function in Small Heat Shock Proteins, The Journal of Biological Chemistry, 2005, pp. 5281-5289, vol. 280, No. 7.

Parcellier, A. et al., HSP27 favors ubiquitination and proteasomal degradation of p27Kip1 and helps S-phase re-entry in stressed cells, The FASEB Journal, 2006, pp. 1179-1181, vol. 20.

Parcellier, A. et al., HSP27 Is a Ubiquitin-Binding Protein Involved in 1-kBa Proteasomal Degradation, Molecular and Cellular Biology, 2003, pp. 5790-5802, vol. 23, No. 16.

Zavadil, J. et al., TGF-B and epithelial-to-mesenchymal transitions, Oncogene, 2005, pp. 5764-5774, vol. 24.

Chapman, HA, Epithlial-mesenchymal interactions in pulmonary fibrosis, Annu Rev Physiol, 2011, pp. 413-435, vol. 73.

Ryhanen, T. et al., Radicicol but not geldanamycin evokes oxidative stress response and efflux protein inhibition in ARPE-19 human retinal pigment epithelial cells, Eur J Pharmacol, 2008 pp. 229-236, vol. 584, No. 2-3 Epub Feb. 14, 2008.

Tanaka, Y. et al., Paclitaxel inhibits expression of heat shock protein 27 in ovarian and uterine cancer cells, International Journal of Gynecological Cancer, 2004, pp. 616-620, Vol. 14, Issue 4.

Yonekura, N. et al., Interferon-gamma dow gulates Hsp27 expresion and suppresses the negative regulation of cell death in oral squamous cell carcinoma lines, Cell Death Differ., 2003, pp. 313-322, vol. 10, No. 3.

Jego, G. et al., Targeting heat shock proteins in cancer, Cancer Lett, 2010, [epub ahead of print].

Mucsi et al., Epithelial-mesenchuymal transition in renal tubular cells in the pathogenesis of progressive tubulo- interstitial fibrosis, Acta Physiol Hung, 2007, pp. 117-131, vol. 94, No. 1-2.

Beckmann, RP et al., Interaction of Hsp 70 with newly synthesized proteins: implications for protein folding and assembly, Science, 1990, pp. 850-854, vol. 248.

Morino M. et al., Specific regulation of HSPs in human tumor cell lines by flavonoids., In Vivo, 1997, pp. 265-270, vol. 11, No. 3.

Al-Shamma, M.R.R. et al., Role of heat shock proteins in the pathogenesis of cystic fibrosis arthritis, Thorax 1997, pp. 1056-1059, vol. 52.

Arrigo, AP et al., Hsp27 (HspB1) and aB-crystallin (HspB5) as therapeutic targets, FEBS Letters, 2007, pp. 3665-3674, vol. 581.

Vidyasagar, A. et al., HSP27 is involved in the pathogenesis of kidney tubulointerstitial fibrosis; Am J. Physiol, 2008, pp. F707-F716, vol. 295.

Micalizzi, D.S. et al., Epithelial-Mesenchymal Transition in Cancer: Parallels Between Normal Development and Tumor Progression, J Mammary Gland Biol Neoplasis, 2010, pp. 117-134.

Karas, J. G. et al., Inhaled antisense oligonucleotide therapies: Inspiration and progress, Drug Discovery Today: Therapeutic Strategies, 2006, pp. 3358-341, vol. 3(3).

Wettstein G., et al. Role of heat shock protein 27 in TGF-β1 induced mesothelial and epithelial to mesenchymal transition (EMT), Sep. 2010, European Respiratory Society, Oral Presentation 211: Stem cells and growth factors in lung injury.

SEQUENCE LISTING

```
<160> NUMBER OF SEQ ID NOS: 13

<210> SEQ ID NO 1
<211> LENGTH: 764
<212> TYPE: DNA
<213> ORGANISM: Homo sapiens

<400> SEQUENCE: 1
ggcacgagga gcagagtcag ccagcatgac cgagcgccgc gtccccttct cgctcctgcg      60
gggccccagc tgggacccct tccgcgactg gtacccgcat agccgcctct tcgaccaggc     120
cttcgggctg ccccggctgc cggaggagtg gtcgcagtgg ttaggcggca gcagctggcc     180
aggctacgtg cgccccctgc ccccgccgc catcgagagc cccgcagtgg ccgcgcccgc     240
ctacagccgc gcgctcagcc ggcaactcag cagcggggtc tcggagatcc ggcacactgc     300
ggaccgctgg cgcgtgtccc tggatgtcaa ccacttcgcc ccggacgagc tgacggtcaa     360
gaccaaggat ggcgtggtgg agatcaccgg caagcacgag gagcggcagg acgagcatgg     420
ctacatctcc cggtgcttca cgcggaaata cacgctgccc cccggtgtgg accccaccca     480
agtttcctcc tccctgtccc ctgagggcac actgaccgtg gaggccccca tgcccaagct     540
agccacgcag tccaacgaga tcaccatccc agtcaccttc gagtcgcggg cccagcttgg     600
gggcccagaa gctgcaaaat ccgatgagac tgccgccaag taaagcctta gcccggatgc     660 ccaccectgc tgccgccact ggctgtgcct ccccgccac ctgtgtgttc ttttgataca     720
```

-continued tttatcttct gtttttctca aataaagttc aaagcaacca cctg                      764

<210> SEQ ID NO 2
<211> LENGTH: 20
<212> TYPE: DNA
<213> ORGANISM: Homo sapiens
<220> FEATURE:
<221> NAME/KEY: misc_feature
<222> LOCATION: (5)..(5)
<223> OTHER INFORMATION: C is methylated
<220> FEATURE:
<221> NAME/KEY: misc_feature
<222> LOCATION: (7)..(7)
<223> OTHER INFORMATION: C is methylated
<220> FEATURE:
<221> NAME/KEY: misc_feature
<222> LOCATION: (10)..(10)
<223> OTHER INFORMATION: C is methylated
<220> FEATURE:
<221> NAME/KEY: misc_feature
<222> LOCATION: (12)..(12)
<223> OTHER INFORMATION: C is methylated
<220> FEATURE:
<221> NAME/KEY: misc_feature
<222> LOCATION: (14)..(14)
<223> OTHER INFORMATION: C is methylated
<220> FEATURE:
<221> NAME/KEY: misc_feature
<222> LOCATION: (17)..(18)
<223> OTHER INFORMATION: 2'-O-methoxyethyl
<220> FEATURE:
<221> NAME/KEY: misc_feature
<222> LOCATION: (20)..(20)
<223> OTHER INFORMATION: 2'-O-methoxyethyl

<400> SEQUENCE: 2
gggacgcggc gctcggucau                                                 20

<210> SEQ ID NO 3
<211> LENGTH: 20
<212> TYPE: DNA
<213> ORGANISM: Artificial Sequence
<220> FEATURE:
<223> OTHER INFORMATION: random control oligonucleotide

<400> SEQUENCE: 3
ccttccctga aggttcctcc                                                 20

<210> SEQ ID NO 4
<211> LENGTH: 21
<212> TYPE: DNA
<213> ORGANISM: Homo sapiens

<400> SEQUENCE: 4
guucaaagca accaccugut t                                               21

<210> SEQ ID NO 5
<211> LENGTH: 21
<212> TYPE: DNA
<213> ORGANISM: Homo sapiens

<400> SEQUENCE: 5
acaggugguu gcuuugaact t                                               21

<210> SEQ ID NO 6
<211> LENGTH: 17
<212> TYPE: DNA
<213> ORGANISM: Homo sapiens

```
<400> SEQUENCE: 6
gcccccatgc ccaagct                                                      17

<210> SEQ ID NO 7
<211> LENGTH: 21
<212> TYPE: DNA
<213> ORGANISM: Homo sapiens

<400> SEQUENCE: 7
ctcgaaggtg actgggatgg t                                                 21

<210> SEQ ID NO 8
<211> LENGTH: 21
<212> TYPE: DNA
<213> ORGANISM: Homo sapiens

<400> SEQUENCE: 8
tggtcggtat gggtcagaaa g                                                 21

<210> SEQ ID NO 9
<211> LENGTH: 23
<212> TYPE: DNA
<213> ORGANISM: Homo sapiens

<400> SEQUENCE: 9
tcagggtcag gatacctctc ttg                                               23

<210> SEQ ID NO 10
<211> LENGTH: 19
<212> TYPE: DNA
<213> ORGANISM: Homo sapiens

<400> SEQUENCE: 10
acagccccgc cttatgatt                                                    19

<210> SEQ ID NO 11
<211> LENGTH: 20
<212> TYPE: DNA
<213> ORGANISM: Homo sapiens

<400> SEQUENCE: 11
cttcggaacc gcttccttca                                                   20

<210> SEQ ID NO 12
<211> LENGTH: 21
<212> TYPE: DNA
<213> ORGANISM: Homo sapiens

<400> SEQUENCE: 12
cgtggttttc tcaccctatg g                                                 21

<210> SEQ ID NO 13
<211> LENGTH: 22
<212> TYPE: DNA
<213> ORGANISM: Homo sapiens

<400> SEQUENCE: 13
ctgggtttct cctcctgttg tc                                                22
```

TREATMENT OF PULMONARY AND PLEURAL FIBROSIS USING HSP27 INHIBITORS

STATEMENT OF RELATED CASE

This application is a continuation of U.S. patent application Ser. No. 13/470,780, now U.S. Pat. No. 8,987,223, filed on May 14, 2012, and claims the benefit of U.S. Provisional Patent Application Ser. No. 61/485,501, filed on May 12, 2011, both of which are incorporated herein by reference.

BACKGROUND OF THE INVENTION

This application related to treatment of pulmonary and pleural fibrosis using inhibitors as hsp27.

Heat shock proteins (HSPs) are a set of highly conserved proteins whose expression is induced by different kinds of stress. Among the different HSPs, HSP27 is highly induced by different stresses such as high temperature, oxidative stress, or anticancer drugs (Beckmann et al., *Science* 1990; 248:850-4; Shashidharamurthy et al., *J Biol Chem* 2005; 280: 5281-9) and is an ATP-independent chaperone. HSP27 is crucial in the control of apoptosis and can act at multiple points in the apoptotic pathways to ensure that stress-induced damage does not inappropriately trigger cell death (Bruey et al., *Nat Cell Biol* 2000; 2:645-52; Jego et al *Cancer Lett*, Nov. 13, 2010, E Pub ahead of print) probably because apoptosis and differentiation are two related processes. Recent reports involve HSP27 in the differentiation process (De Thonel et al., *Blood* 2010, 116:85-96). The cytoprotective function of HSP27 is also explained by its behavior as a molecular chaperone for other cellular proteins. Inappropriate activation of signaling pathways could occur during acute or chronic stress as a result of protein misfolding, protein aggregation, or disruption of regulatory complexes. The action of chaperones, through their properties in protein homeostasis, is thought to restore the balance. In association with HSP27 chaperone function, it has been demonstrated that HSP27 under stress conditions play a function in "proteins triage"; HSP27 may either stabilize or accelerate the degradation by the proteasome of certain "client" proteins to assure the survival of the cell (De Thonel et al 2010; Andrieu et al. *Oncogene* 2010, 29: 1883-1896; Parcellier et al., *FASEB J* 2006, 20: 1179-1181, and Parcellier et al., *Mol Cell Biol* 2003, 23: 5790-5802). The strong cytoprotective function of HSP27 together with the fact that the protein is overexpressed in most cancer combine to make this chaperone an interesting target to inactivate in cancer therapy. In this way, HSP27 depletion in different animals' models induces the regression of the tumors. The second generation oligonucleotide, OGX-427, is a specific inhibitor of HSP27 that can be administered in patients. Its anti-tumor effect has been demonstrated in many animal experimental models and it is now being tested in phase I/II clinical trials as a chemosensitizing agent in prostate cancer.

Epithelial-to-mesenchymal transition (EMT) occurs when epithelial cells transdifferentiate and acquire a myofibroblastic phenotype (Chapman H A., *Annu Rev Physiol* 2011; 73:413-35) TGF-β1, one of the most potent profibrotic mediators characterized so far, is also considered to be a master switch for the induction of EMT in various organs including the lung (Zavadil et al., *Oncogene* 2005; 24:5764-74). EMT is known to be involved in a variety of normal physiological processes including gastrulation, heart formation, and palate closure during embryogenesis but also in pathological conditions such as fibrosis, cancer invasion and metastasis. EMT describes a phenotypic change characterized by the loss of epithelial markers including E-cadherin and cytokeratin, the gain of mesenchymal markers such as α-smooth muscle actin (α-SMA), and the acquisition of cell migration properties. It has been reported that the cells migrate across the damaged basement membrane to the interstitial space, where they become activated myofibroblasts. (Mucsi et al. *Acta Physiol Hung* 2007; 94:117-31) The presence of α-SMA represents the most reliable marker of the myofibroblastic phenotype. The mechanisms leading to EMT are still poorly known.

Fibrosis generally is the formation of fibrous tissue as a reparative or reactive process. Pathological fibrosis is the undesirable formation of fibrous tissue that is associated with a disease state. In many instances, treatment options for fibrosis are presently limited or unavailable. For example, among fibrotic disorders, idiopathic pulmonary fibrosis (IPF) is a devastating disease characterized by a progressive and exaggerated extra-cellular matrix (ECM) accumulation and structural changes resulting in restrictive impairment of lung functions. The disease has no known etiology although some anti-cancerous drugs (e.g. bleomycin) are well known triggering events for the initiation of pulmonary fibrosis. (www-.pneumotox.com. The drug-induced lung diseases. [Website] 2011 July, 2002 [cited 1996]).

The development of IPF is classically thought as an abnormal alveolar repair and myofibroblasts are the main cellular components responsible for the tissue remodeling that occurs during this repair. The pathological changes in IPF typically start in subpleural lung regions. (American Thoracic Society. *Am J Respir Crit Care Med* 2000; 161:646-64) This subpleural predominance of fibrosis is even a characteristic feature of IPF. To date, there is no clear explanation for this. Cool et al. suggest that myofibroblasts form a network, a "fibroblastic reticulum," extending progressively from the pleura to the underlying parenchyma. (Cool et al., *Am J Respir Crit Care Med* 2006; 174:654-8. We recently reported that over expression of the fibrogenic cytokine transforming growth factor (TGF)-β1 in the pleural space not only induces progressive pleural fibrosis, but also is associated with abnormal collagen deposition within the subpleural lung parenchyma as observed in IPF. We demonstrated in this model that mesothelial cells undergo a transformation similar to what is observed during EMT in the presence of TGF-β and that these mesenchymal cells migrate and invade the lung parenchyma, suggesting that mesothelial cells may play a key role in IPF (Decologne, et al. *J Immunol* 2007; 179; 6043-6051).

US Patent Publication No. 2006/0003954 discloses an antisense inhalation therapy for IPF and other lung diseases in which the antisense is targeted to wild type COL1A.

U.S. Pat. No. 6,887,853 discloses treatment for fibrogenic disease using geldanamycin, which is an HSP90 inhibitor. No mention is made of HSP 27. Ryjänen et al. *Eur J Pharmacol.* 2008 Apr. 28; 584(2-3):229-36. Epub 2008 Feb. 14 discloses that geldanamycin increases HSP27 levels. HSP27 is also known for providing anti-inflammatory properties leading to increases in IL-10 and IL-12. (See US Patent Application No. 2001/004971). Since inflammation may be implicated in IPF and other forms of fibrosis, (See, Wilson et al, *Mucosal Immunol.* 2009 March; 2(2): 103-121), this combination of teachings would seem to suggest that reduction of HSP27 would be ill-advised in the treatment of fibrosis, including IPF.

SUMMARY OF THE INVENTION

It has been surprisingly found that reduction of HSP27 expression is in fact beneficial in the treatment of pulmonary fibrosis and in particular subpleural fibrosis and IPF. Thus, in accordance with a first aspect of the present invention there is provided a method for treating pulmonary fibrosis comprising administering to an individual in need of treatment for pulmonary fibrosis an inhibitor of HSP27.

In a further aspect, the present invention provides a pharmaceutical composition for treatment of pleural or pulmonary fibrosis comprising an inhibitor of HSP27 and a pharmaceutically acceptable carrier. This composition may be for use in the treatment of idiopathic pulmonary fibrosis (IPF); or any one of pleural fibrosis, subpleural fibrosis, pulmonary fibrosis, Usual Interstitial Pneumonia (UIP) or drug-induced lung fibroses.

The inhibitor in the pharmaceutical composition is suitably selected from the group consisting of nucleotide inhibitors, peptide and antibody inhibitors, and small molecule inhibitors, for example a nucleotide inhibitor of HSP27 such as Seq ID No. 2.

The pharmaceutical composition is suitably configured for administration by way of inhalation; or by way of any one of intra-pleural injection, intravenous injection or intra-tracheal administration and the form of the composition and pharmaceutically acceptable are selected for this purpose. One specific suitable carrier comprises phosphate buffered saline.

The invention further encompasses use of an inhibitor of HSP27 or a pharmaceutical composition comprising an inhibitor of HSP27 and a pharmaceutically acceptable carrier in the treatment of pleural or pulmonary fibrosis and a method of such treatment. Such use of method may be for the treatment of idiopathic pulmonary fibrosis (IPF); or any one of pleural fibrosis, subpleural fibrosis, pulmonary fibrosis, Usual Interstitial Pneumonia (UIP) or drug-induced lung fibroses.

The invention also encompasses the use of an inhibitor of HSP27 in the manufacture of a medicament for the treatment of pleural or pulmonary fibrosis as described herein.

DETAILED DESCRIPTION OF THE INVENTION

Figure 1A:
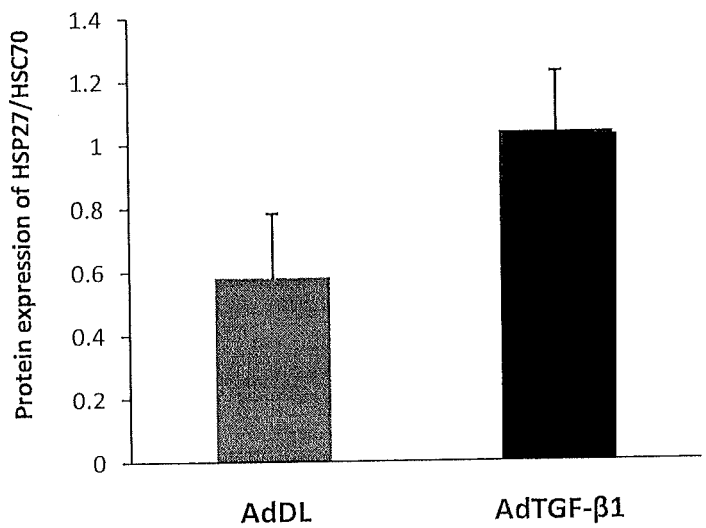
FIG. 1A shows the increased expression of HSP27 following infection of lung cells with a vector encoding TGF-β1 (AdTGF-β1)
Figure 1B:
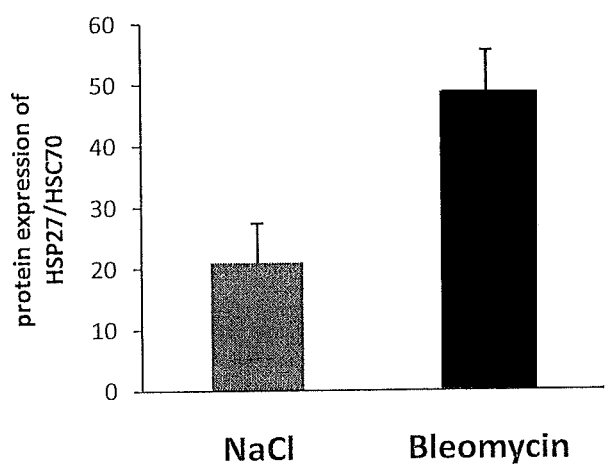
FIG. 1B shows the increased expression of HSP27 following intra-tracheal administration of bleomycin to mice. Western blot was performed on whole lung protein extracts from mice receiving during 21 days either NaCl or Bleomycin. HSC70 is used as a loading control, and the amounts were evaluated by densitometry.

The present inventors have determined, as exemplified below, that HSP27 is involved in pulmonary and pleural fibrosis, and that targeting HSP27 in vitro or in vivo inhibits TGF-β1-induced fibrosis. The present inventors have also shown that HSP27 expression is linked to endothelial to mesenchymal and mesothelial to-fibroblastoid transitions ((collectively EMT), and that mesothelial cells are highly susceptible to undergoing EMT suggesting they are very aggressive and sensitive cells in the process of EMT and therefore of pleural and pulmonary fibrosis. Furthermore, in IPF lung tissue, HSP27 is expressed at high level in clusters of bronchiolar basal cells precisely localised within fibroblast foci, wedged between luminal epithelial cells and myofibroblasts where EMT is supposed to occur. (Chilosi et al. *Respir Res* 2006; 7:95; Korfei et al., *J Proteome Res.* 2011, Mar. 29 E Pub ahead of print). Our work here shows that HSP27 is overexpressed during pleural/pulmonary fibrosis development most probably though its implication in TGF-β1-induced EMT. Further, we demonstrate that HSP27 overexpression on its own is sufficient to induce EMT. Interestingly, the function of HSP27 does not seem restricted to mesothelial cells undergoing EMT but most probably also concerns epithelial cells as we demonstrate in A549 cells.

Taken together, these results support the validity of the present invention, in which reduction of HSP27 is used in the treatment of pulmonary and pleural fibrosis.

DEFINITIONS

The term "HSP27" refers to heat shock protein 27, an approximately 27 kilodalton stress-induced protein. HSP27 is also sometimes referred to as heat shock protein beta-1 (HSPB1). The sequences of HSP27 are known in the art for *Homo sapiens* (AB020027, X54079, NM_006308, NM_001540 and NM_001541), dogs (NP_001003295), cattle (NP_001020740), mice (NP_038588) and other species. A sequence for human HSP27 is provided as Seq ID No. 1.

The term "inhibitor" or "inhibition" of HSP27 refers to a composition or action that leads to a reduction in the amount of active HSP27. The reduction may occur at the expression level, or through post-expression/post-translation inactivation of HSP27. Examples of inhibitors includes nucleotide compounds targeting HSP27, peptide aptamers (Gilbert et al, Oncogene. 2011 Mar. 21. [Epub ahead of print]); flavonoid inhibitors of HSP27, antibodies that interact with HSP27 (Tezel and Wax, *J. Neuroscience* 10:3553-3562 (2000), and interferon-γ which has been shown to downregulate expression of HSP27. (Yonekura et al., (2003) Cell Death and Differentiation 10, 313-322).

The terms "treatment" or "treating" refer to the administration or use of an HSP27 inhibitor for the purpose of obtaining a therapeutic benefit in an individual in need for treatment for pulmonary fibrosis. The therapeutic benefit may be a reduction in the severity of existing fibrotic condition, a slowing of the progression of an existing fibrotic condition or the delay in onset of a potential fibrotic condition. The term 'therapeutically effective amount" refers to an amount that is reasonably expected to achieve such a therapeutic benefit, even if no benefit is discernable in a particular treated individual.

The term "individual" refers to a living mammal being treated. In specific embodiments, the individual is a human, although treatment in other mammalian species, particularly pet and agricultural species such as dogs and cattle is within the scope of the invention.

The term "pleural and pulmonary fibrosis" refers to pathological fibrosis of the lungs whether arising from disease or injury. The term encompasses IPF, pleural fibrosis, subpleural fibrosis, pulmonary fibrosis, Usual Interstitial Pneumonia (UIP) and drug-induced lung fibroses.

Inhibitors of HSP27

In the methods and pharmaceutical compositions of the invention, an inhibitor of HSP27 is used.

In accordance with some embodiments, the HSP27 inhibitor is a nucleotide inhibitor. Examples of nucleotide inhibitors include antisense sequences, which may be full-length antisense (see Horman et al., *Int. J. Cancer* (1999) 82: 574-582), or shorter oligonucleotide sequences, having a length of 100 bases or less, for example 12 to 30 bases. Such antisense species are complementary to the target HSP27 gene to an extent sufficient to achieve antisense inhibition in vivo, and may include degeneracy to take into account allelic variation. Specific oligonucleotide antisense inhibitors of HSP27 are known in the art from US Patent Publications 2004/0127441, 2009/0264502

In specific embodiments, the HSP27 inhibitor is OGX-427, an antisense oligonucleotide made by OncoGenex that is currently in clinical trials for treatment of various types of cancer. OGX-427 is a 4-12-4 2'-MOE gapmer oligonucleotide with phosphorothiolated internucleotide linkages which can be represented as (Seq. ID No. 2)

where G, A, MeC, and T represent the nucleosides 2'-deoxyguanosine, 2'-deoxyadenosine, 2'-deoxy-5-methylcytidine, and 2'-deoxythymidine, the underlined nucleosides denote 2'-O-methoxyethyl (2'-MOE) modifications of the nucleosides, and the internucleotide linkages are phosphothioate diester, sodium salts.

In other embodiments, the nucleotide HSP27 inhibitor is a double stranded RNA species (or precursor) that operates by an siRNA mechanism to reduce expression of HSP27. Specific RNA species for this purpose are known from US Patent Publication 2004/0127441, and Chauhan, et al. (2003) *Cancer Res.* 63, 6174-6177.

Peptide aptamers (Gilbert et al, Oncogene. 2011 Mar. 21. [Epub ahead of print]); and antibodies (Tezel and Wax, *J. Neuroscience* 10:3553-3562 (2000) that interact with HSP27 are also known and could serve as inhibitors of HSP27 in accordance with the invention. Other peptides that bind to HSP27, such as CP91 or binding fragments thereof as described in US Patent Publication No. 2007/0003555 could also be employed.

Cytokines such as interferon-γ are also known to inhibit HSP27 and can be used as inhibitors in the present invention. Yonekura et al., *Cell Death and Differentiation* (2003) 10: 313-322.

Other inhibitors of HSP27 are also known which are generally "small molecule" inhibitors. These include flavonoids such as quercetin, (Morino et al., in vivo (1997) 11: 265-270; JP 10045572, JP 10045574, JP10036261 and JP 10036267), and biphenyl isooxazoles such as 5-(5-Ethyl-2-hydroxy-4-methoxyphenyl)-4-(4-methoxyphenyl)isoxazole (KRIBB3) (Shin et al. *The Journal of Biological Chemistry* VOL. 280, NO. 50, pp. 41439-41448, Dec. 16, 2005). KRIBB3 is available commercially from Sigma-Aldrich is understood to reduce HSP27 activity by acting as a specific inhibitor ($IC_{50}$ of 50 nM) of PKC-dependent phosphorylation of HSP27. Berberine derivatives have also been shown to inhibit hsp27. (EP 0 813 872) Paclitaxel has also been shown to be an inhibitor of hsp27 expression. (Tanaka et al., Int J Gynecol Cancer. 2004 July-August; 14(4): 616-20).

Administration and Formulation

The methods of the present invention involve administration of an HP27 inhibitor as described above to an individual in need of treatment, or the incorporation of the inhibitor into a pharmaceutical composition suitable for administration. As will be appreciated, the mode of administration and the pharmaceutical carrier employed will vary depending on the specific inhibitor and the condition for which the treatment is intended.

In general, administration may be by any known approach including intravenous, oral, intramuscular, intranasal, or inhaled. In specific embodiments, administration is suitably regional to the area to be treated, i.e. the lungs. For example, inhalation is one mode of regional administration. Inhalation strategies for antisense therapeutics are known, for example from Karras et al, *Drug Discovery Today: Therapeutic Strategies* (2006) 3(3): 335-341 and Crosby et al, *J Pharmacol. and Exp. Therapeutics*. (2007) 321: 938-946. See also, US Patent Publication No. 2006/0003954. Other modes of regional administration to the lungs include intra-pleural injection and intra-tracheal administration.

In one method, the HSP27 inhibitor is an antisense oligonucleotide. One such product is a compound called "OGX-427" which is currently provided to patients at about 600 mg per patient in a 25 mg/mL concentration formulated as a mannitol-phosphate buffer solution (pH 7.4) for IV administration. OGX-427 dosing solutions are administered intravenously using an infusion pump. In some situations, the administration will be preceded or accompanied by administration of an antihistamine.

Experimental Results

Materials and Methods

Recombinant Adenovirus and Antisense Oligonucleotides

For experiments on pleural fibrosis we used AdTGF-β1223/225, an adenovirus construct with a mutant TGF-β1 translated into spontaneously bioactive TGF-β1 (AdTGFβ1) and control vectors (AdDL) with no insert in the deleted E1 region. The construction of adenoviral vectors is described in detail elsewhere (DeCologne, 2007, supra; Bett et al. *Proc Natl Acad Sci USA* 1994; 91:8802-6; Sime et al., *J Clin Invest* 1997; 100:768-76)

OGX427 (SEQ ID No: 2), a second-generation AntiSense Oligonucleotids targeting Hsp27, was provided by OncoGeneX (Vancouver Canada). A control oligonucleotide having the sequence CCTTCCCTGAAGGTTCCTCC (SEQ ID No: 3) was obtained from Martin Gleave at the Prostate Cancer Center, Vancouver Canada and is also known as ISIS 141923.

Animal Treatment

Female Sprague-Dawley rats (Charles River Laboratories) weighing 200-225 g were housed in special pathogen-free conditions. Rodent laboratory food and water were provided ad libitum. The animals were treated in accordance to the guidelines of the Ministère de la Recherche et de laTechnologie (Paris, France). All experiments were approved by the Comité d'Ethique de l'Université de Bourgogne (Bourgogne, France). All animal procedures were performed with inhalation anesthesia with isoflurane (TEM, Lormont, France). Adenovector administrations were performed by intrapleural injection in 800 µl of NaCl 0.9% containing a total of $1.3 \times 10^9$ PFU AdTGF-β1, AdDL or AdLacZ. The intrapleural injection protocol was described in details elsewhere (DeCologne, 2007, supra)).

12 mg/kg of control ASO and OGX-427 were daily administrated by intrapleural injection during 5 days after adenoviral administration. Rats were euthanized by abdominal aortic bleeding and lungs were harvested and processed following what was previously described in Decologne et al (DeCologne, 2007, supra)).

For primary cell harvesting, 8 ml of HBSS (Lonza, Paris, France) were injected in the pleural cavity through the diaphragm then removed and followed by a 10 ml trypsin 5%, EDTA 0.4% administration for 30 min. This lavage was removed and placed in 30 ml of DMEM (Dulbecco's Modified Eagle Medium, Lonza) with 15% FBS (Fetal Bovine Serum, Lonza). After centrifugation (1300 rpm, 5 minutes), the cell pellet was re-suspended into 5 ml DMEM, FBS 15% and placed at 37° C., 5% $CO_2$.

For lung tissue or histological analysis after intratracheal administration of bleomycin in mice or AdTGF-β1 in rats we used material from previous experiments (respectively Decologne et al, *Eur Respir J* 2010; 35:176-85, and Bonniaud et al. *Am J Respir Crit Care Med* 2005; 171: 889-98).

Histology

Immunohistochemitry: Inflated lungs were transversally cut and paraffin embedded. 5 µm section were performed and stain with primary antibodies (Ab), Mouse monoclonal anti-α-SMA (Sigma, St Quentin Fallavier, France, 1/200), rabbit polyclonal anti-HSP27 (EnzoLife Science, Villeurbanne, France, 1/200) and rabbit polyclonal cleaved caspase 3 (cell signaling, Saint Quentin, France, 1/100). Secondary Abs used were respectively, a goat anti-mouse IgG biotin conjugated and a goat anti-rabbit IgG biotin conjugated. After peroxidase inhibition (PBS plus H2O2, 20 min), lung section were incubated over night at 4° C. with primary ab. Tissue section were after PBS 1× (Phosphate Buffer Saline) wash incubated with the secondary ab (1/500) 45 min. The streptavidin-HRP complex (Jackson ImmunoResearch Laboratories, PA, USA, 1/500) was used 45 min at room temperature. 3-Amino-9-ethylcarbazole/hydrogen peroxide was used as chromagen substrate. Slides were counterstained with hematoxylin.

Cytochemical staining for β-galactosidase was performed as described in DeCologne, 2007, supra.

Determination of TGF-β1 Level in PLF

Total human TGF-β1 was determined from pleural lavage fluid (PLF) using ELISA (R&D Systems, Lille, France), performed according to the recommendations of the manufacturer. The sensitivity of this assay was 7 pg·mL-1.

Cell Culture

Mesothelial rat primary cells were grown in Dulbecco's Modified Eagle's Medium (DMEM) 1% L-glutamine, 1% penicillin-streptomycin with 15% Fetal Bovine Serum (FBS. Lonza, Paris, France). Cells were assessed before culture and from passage 1 to 4.

Mesothelial rat established cell line 4/4 RM4 cells (American Type Culture Collection—ATCC—Rockville, Md.) were seeded in Ham's F10 (Lonza), with FBS 15%. Mesothelial human established cell line MET-5A (ATCC) were seeded in Medium 199 (lonza), 1% L-glutamine, 1% penicillin-streptomycin with 10% FBS. Epithelial human cell line A549 cells (ATCC) and were seeded in Ham's F10 (lonza) with 10% FBS.

For EMT induction and analysis, all the different cells were exposed to their respective medium containing 10 ng/ml recombinant (r)TGF-β1 (R&D system, Lille, France) for 6, 12, 24, or 48 hours.

RNA Interference

HSP27 siRNA were purchased from applied bios system (Courtaboeuf, France). The sense and antisense sequence were respectively: 5'-GUUCAAAGCAACCACCUGUtt-3 (SEQ ID No: 4)' and 5'-ACAGGUGGUUGCUUUGAACtt-3'. (SEQ ID No: 5). They were used at a concentration of 50 nM. SiRNA were transfected using INTERFERin (polyplus, Illkirch, France) following the manufacturer recommendations. 5-6 hours after transfection medium were changed and cells were treated or not with 10 ng/ml TGF-β1 for 12, 24 or 48 hours. Seq ID No. 3 was used as a random control oligonucleotide.

Transfection

HSP27 transfection was made using a pcDNA6 plasmid encoding human HSP27 as previously described. (Bruey et al. *Nat Cell Biol* 2000; 2:645-52) Transfections were performed using OptiMEM (Invitrogen, Cergy pontoise, france) media and Nanojuice transfections reagent (Novagen, Merck KGaA, Darmstadt, Germany). Cells were lyzed 6, 9, 12, 24 or 48 h after transfections.

Heat Shock

Cells were placed in 42° C. water for 30 min and placed back at 37° C., 5% $CO_2$, 6 hours before protein or RNA analysis.

Western Blot

Protein extraction was made using triton X 100 during 30 min at 4° C., vortexing every 10 min. Protein dosage is made with the modified lowry kit (Biorad, Marne-la-Coquette, France). Equal amounts of protein (30-50 µg) were electrophoresed through 8 to 12% SDS polyacrylamide gels. The separate protein bands were transferred onto a PVDF membrane. The non-specific sites were saturated with a solution of PBS-tween 0.1%, nonfat milk 8%. Membranes were incubated with primary Abs over night at 4° C. Secondary Abs IgG linked to HRP (HorseRadish Peroxidase, Jackson ImmunoResearch Laboratories, PA, USA) were used at a concentration of 1/5000. Enhanced ChemiLuminescent substrat (ECL, santa cruz biotechnology, CA, USA) was used to detect the protein of interest. Primary Abs were ?-SMA mouse monoclonal Ab (Progen, 1/1000), a HSP27 Rabbit polyclonal Ab (Enzo life science, Villeurbanne, France; 1/2000), E-cadherin mouse monoclonal Ab (R&D systems, 1/1000), PAI-1 was mouse monoclonal Ab (thermo scientific, 1/1000), SMAD2, phosphoSMAD3, TGF-?1 were rabbit polyclonal Abs (cell signaling, Saint Quentin, France, 1/1000), SMAD3 was rabbit polyclonal Ab (thermo fisher, Illkirch, France; 1/1000), HSC70 was a mouse monoclonal ab (santa cruz biotechnology, CA, USA; 1/10000), rhoA was mouse monoclonal Ab (cytoskeleton, Denver, USA; 1/1000), calretinin was a mouse monoclonal Ab (santa cruz biotechnology, CA, USA; 1/1000), cytokeratin was a mouse monoclonal Ab (affinity, 1/1000).

Co-Immunoprecipitation

Santa Cruz Protein G-sepharose were incubated at 4° C. on well with HSP27 polyclonal Ab during 90 min. Extracted proteins from Met-5A or A549 were add to the sepharose/Ab mix and incubated on well over night at 4° C. The mixture was centrifuged 5 min and the resulting pellet was washed three times with the lysis solution. Western blots were performed on the immunoprecipitated proteins.

Immunofluorescence

Cells were fixed with ParaFormaldehyde (PFA) 4% solution and permeabilized with PBS-triton 0.1% solution. Saturation of non specific sites was made with BSA 5%. Cells were incubated with primary Abs at 1/200 over night in humid chamber at 4° C. Cells were stained for α-SMA (Sigma, 1/200), HSP27 (Enzo life science, Villeurbanne, France; 1/200), E-cadherin (BD System, Le Pont-de-Claix, France, 1/100), Calretinine (santa cruz technology, CA, USA; 1/200), F-actin (phalloidin, 1/300).

As secondary Abs Alexa-488 and Alexa-568 conjugated goat anti-mouse or goat anti-rabbit were used at 1/2000. DAPI was used to stain nucleus. Photos were taken with x64 objective (Zeiss, Le Pecq, France).

Quantitative RT-PCR

Total RNA was extracted using TRIzol (Invitrogen, Cergy Pontoise, France) from MET-5A and A549 cells treated or not with rTGF-β1 12 or 24 hours and transfected or not by HSP27 siRNA or plasmid encoding HSP27. Reverse transcription was performed on the total RNA using the M-MLV kit (Promega, Charbonnieres, France). Quantitative RT-PCR was performed on the cDNA using the SYBR green master mix (promega, Charbonnieres, France). The sense and antisense primers for HSP27 were 5'-GCCCCCATGC-CCAAGCT-3' (SEQ ID No. 6) and 5'-CTCGAAGGT-GACTGGGATGGT-3' (SEQ ID NO: 7), respectively. The sense and antisense primers for α-SMA were 5'-TGGTCG-GTATGGGTCAGAAAG-3' (SEQ ID No: 8) and 5'-TCAGGGTCAGGATACCTCTCTTG-3' (SEQ ID No: 9), respectively. The sense and antisense primers for E-cadherin were 5'-ACAGCCCCGCCTTATGATT-3' (Seq ID No. 10) and 5'-CTTCGGAACCGCTTCCTTCA-3' (Seq ID No. 11), respectively. The sense and antisense primers for PAI-1 were 5'-CGTGGTTTTCTCACCCTATGG-3' (Seq ID No. 12) and 5'-CTGGGTTTCTCCTCCTGTTGTC-3' (Seq ID No: 13) respectively.

Statistical Analysis

Comparisons between groups were performed by the Mann-Whitney test and comparisons between animals in the same group by the Wilcoxon test.

Results

HSP27 is Overexpressed During Lung Fibrosis In Vivo

Rats receiving an adenovirus encoding for TGF-β1 (AdTGF-β1) by intrapleural or intratracheal injection developed, as previously published, pleural/subpleural (DeCologne, 2007, supra) and parenchymal fibrosis (Sime et al, supra), respectively. We demonstrated here by immunohistochemistry and western blot analysis of pulmonary tissue that HSP27 together with the well-known mesenchymal/fibrosis marker, α-SMA were strongly expressed in animals that have been treated with AdTGF-β1 and that developed a fibrosis. Both proteins co-localized in fibrotic areas. In contrast, hardly any expression of α-SMA and HSP27 was observed in the control animals that received an empty adenovirus AdDL and that did not develop a fibrosis. These results were confirmed in another pulmonary fibrosis model. Intratracheal administration of bleomycin in mice is a classical animal model of fibrosis that reproduces the acute lung injury found in patients. We observed that paralleling fibrosis formation, bleomycin intra-tracheal administration induced a significant HSP27 overexpression which was concomitant with the induction of the mesenchymal marker α-SMA, as assessed by immunoblotting in animals' lung tissue (FIGS. 1A and B)

HSP27 is a well known anti-apoptotic protein (Bruey et al, Nat Cell Biol). However, HSP27 overexpression in this fibrotic context could not be associated with apoptosis since the small amount of apoptotic mesothelial and epithelial cells found was identical in lung tissues overexpressing HSP27 and developing a fibrosis than in those from control animals that do not develop a fibrosis and with a HSP27 expression very weak. Thus, the overexpression of HSP27 seemed related to other fibrotic triggering events.

Mesothelial Cells are Prone to Undergo EMT In Vitro

Figure 2A:
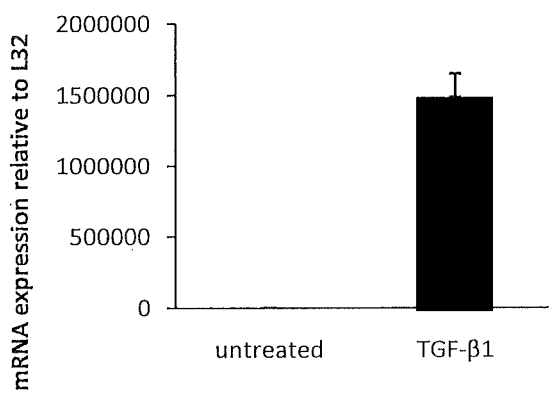
FIGS. 2A-C show mRNA levels for HSP27, α-SMA, and E-cadherin, respectively, after treatment of human mesothelial Met-5A cells with rTGF-β1 at a concentration of 10/ng/ml for 48 h as compared to untreated controls. RNA expression levels were analyzed by PCR. Bars, SD (n=4).
Figure 2B:
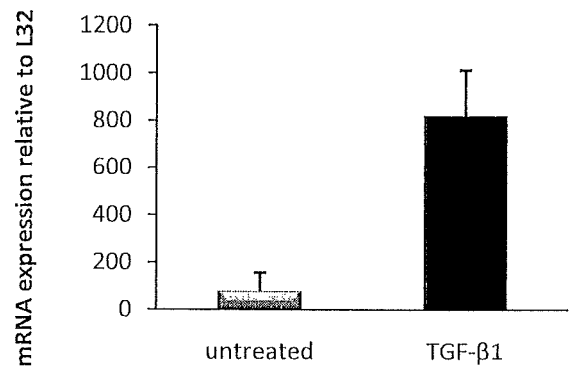
Figure 2C:
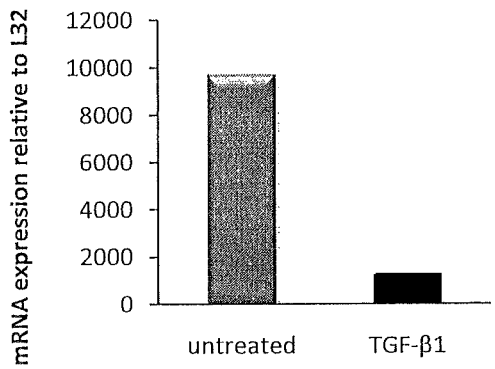
Figure 2D:
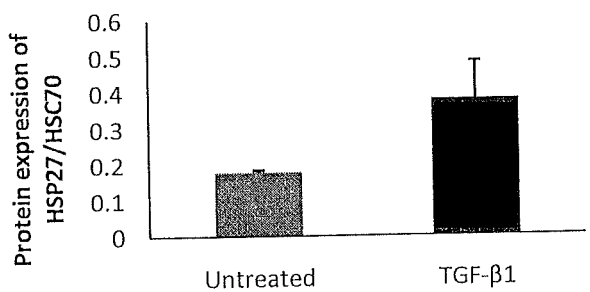
FIG. 2D-F protein levels for HSP27, α-SMA, and E-cadherin, respectively, after treatment of human mesothelial Met-5A cells with rTGF-β1 at a concentration of 10/ng/ml for 48 h as compared to untreated controls. RNA expression levels were analyzed by PCR. Bars, SD (n=4).
Figure 2E:
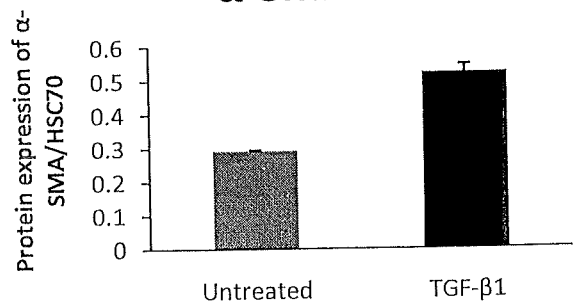
Figure 2F:
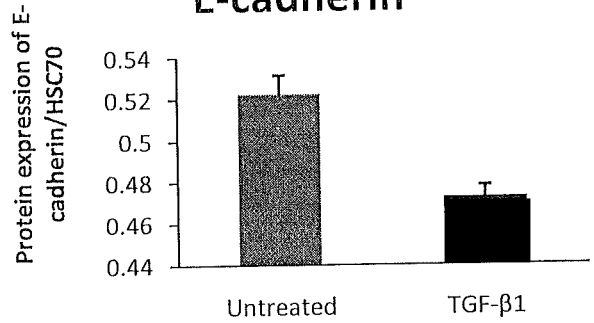

We previously demonstrated that during fibrosis induced by adenoviral TGF-β1 infection in rodents, pleural mesothelial cells were able to trans-differentiate and acquire myofibroblast proprieties that included α-SMA expression and the ability to migrate into the pulmonary parenchyma. This particular process in which the starting cells were not epithelial but mesenchymal, seemed essential for pleural and pulmonary fibrosis. To study whether we could reproduce in vitro this process, we cultivated human Met-5A and rat 4/4 RM4 mesothelial cells in the presence of recombinant TGF-β1. These cells were able to go in culture through this process as demonstrated, both at the RNA and protein level, by the increase in α-SMA expression (FIGS. 2B and 2E) and the concomitant loss in E-cadherin expression (FIGS. 2C and 2F).

We next confirmed this in vitro process in primary mesothelial cells extracted from rats. In contrast to the established mesothelial cell lines, primary mesothelial cells did not need rTGF-β1 to undergo EMT, but they seem to "trans-differentiate" spontaneously as they went through culture passages. Immediately after extraction from the rats, primary mesothelial cells expressed epithelial markers such as cytokeratin or E-cadherin and the mesothelial marker calretinin, but they did not express the mesenchymal marker α-SMA. After the first passage, these primary mesothelial cells started to express α-SMA. After two passages, they did not express cytokeratin anymore whereas α-SMA expression progressively increased over passages and that of E-cadherin decreased. Moreover, while at passage number 1 mesothelial cells had the expected flattened ovoid shape, at passage number 4 they acquired a strong fibroblastoïd like shape. The mesothelial marker calretinin was used as a control for the absence of fibroblasts contamination in the culture. All together, we provide evidence that mesothelial cells undergo EMT in vitro.

HSP27 Expression Increases During EMT as Myofibroblats Features Appear and Associates with α-SMA Because HSP27 was overexpressed in fibrotic areas in vivo and EMT is important in the fibrotic process, we hypothesized that HSP27 may play a role in the process of EMT. We next studied HSP27 expression during the above mentioned EMT process in vitro. We found, both in primary mesothelial cells and in the human mesothelial cell lines undergoing EMT, that HSP27 expression increased, at the RNA (FIG. 2C) and protein level, as the cells started expressing the myofibroblast marker α-SMA. Immunofluorescence experiments demonstrate that both HSP27 and α-SMA colocalized during rTGF-β1-induced EMT in human cultured mesothelial cells and that these two proteins associated. These results were confirmed in vivo in our fibrosis model. Immunofluorescence and immunohistochemistry staining showed that HSP27 and α-SMA colocalized in fibrotic areas during pleural and pulmonary fibrosis.

This HSP27 overexpression was not just specific of mesothelial cells undergoing EMT but was also found during the classical EMT involving epithelial cells. HSP27 was found to be overexpressed, coincidentally with the expression of α-SMA, in epithelial A549 cells during rTGF-β1-induced EMT. (Kasai et al. *Respir Res* 2005; 6:56) Thus, during TGF-β1-induced EMT, HSP27 was overexpressed paralleling the appearance of α-SMA with which it associated.

HSP27 Overexpression Induces an EMT Process in Mesothelial Cells Probably Through TGF-β1 Induction and α-SMA Stabilization To study the involvement of HSP27 in the EMT process, we induced the overexpression of HSP27 in the human mesothelial Met-5A cells by three different methods: heat shock, staurosporine treatment, and transfection with a plasmid encoding HSP27. As expected, a heat shock (30 min at 42° C. followed by 6 h incubation at 37° C. to allow HSP expression) and a cytotoxic agent like staurosporine were efficient inducers of HSP27. (Brunet Simioni et al., *Oncogene* 2009; 28:3332-44) A more specific overexpression was obtained by HSP27 cDNA transfection. Whatever the method used, HSP27 overexpression resulted in an increase in α-SMA expression/content. Conversely, siRNA-meditated depletion of HSP27 inhibits rTGF-β1 induced α-SMA in human endothelial Met-5A cells and epithelial A549 cells. This decrease in α-SMA content induced by HSP27 depletion seems to be, at least in part, the result of its proteasomal degradation because in the presence of an inhibitor of the proteasome, such as MG132, α-SMA levels were restored Transfection-induced HSP27 overexpression was not only able to increase the content in α-SMA but also reproduced other EMT features induced by TGF-β1. HSP27 gene transfer (without any rTGF-β1) was associated with a decrease in E-cadherin expression and, immunofluorescence staining showed that HSP27 overexpression leads to the formation of α-SMA fibers with an even stronger organization than that induced by TGF-β1 treatment. In contrast, depletion of HSP27 by means of a specific siRNA blocks rTGF-β1-induced E-cadherin down-regulation and α-SMA upregulation.

We next further compared EMT induced by HSP27 overexpression with that induced by TGF-β1. In mesothelial Met-5a cells and in A549 epithelial cells, transfection-induced HSP27 overexpression was able to induce TGF-β1 and, thereby, we also observed an increase in the proteins that participate in TGF-β1 signal transducing pathway (i.e. Smad2 and Smad3 and the anchor protein SARA). Moreover, genes whose expression is known to be modulated by TGF-β31, like α-SMA and PAI-1 (upregulated by TGF-β1) or E-cadherin (downregulated by TGF-β1) seem identically modulated by HSP27 overexpression (FIGS. 3A to 3F). Altogether, we conclude that HSP27 overexpression might induce an EMT in mesothelial cells through its effect inducing the production of TGF-β1 and, most probably, by its chaperon function stabilizing α-SMA protein.

HSP27 Inhibition Blocks EMT in Cultured Cells

Figure 3A:
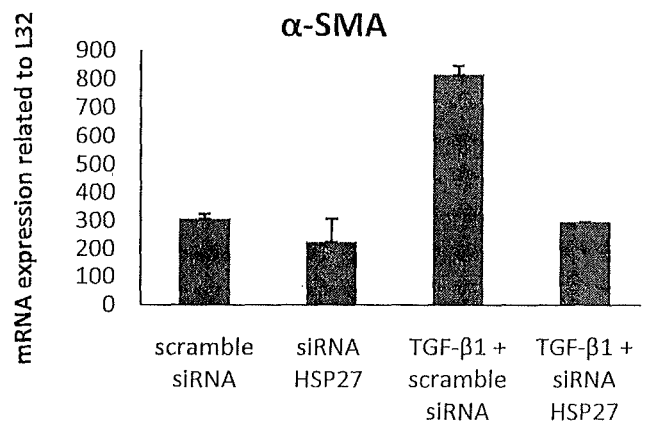
FIGS. 3A-C show mRNA levels for α-SMA, E-cadherin and PAI-1, respectively, after treatment with a scrambled siRNA control, anti-HSP27 siRNA, scrambled siRNA control plus rTGF-β1, or anti-HSP27 siRNA plus rTGF-β1 ((10 ng/ml, 48 h)). Bars, SD (n=4).
Figure 3B:
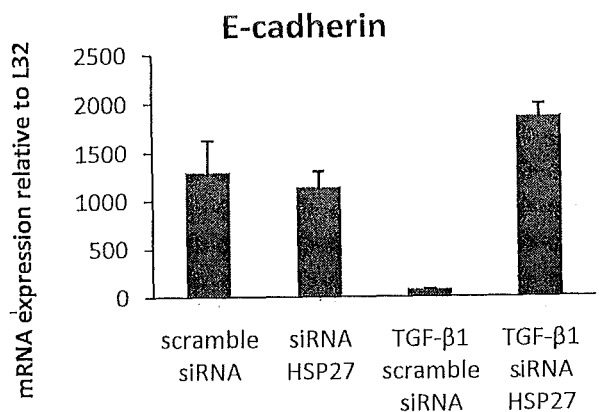
Figure 3C:
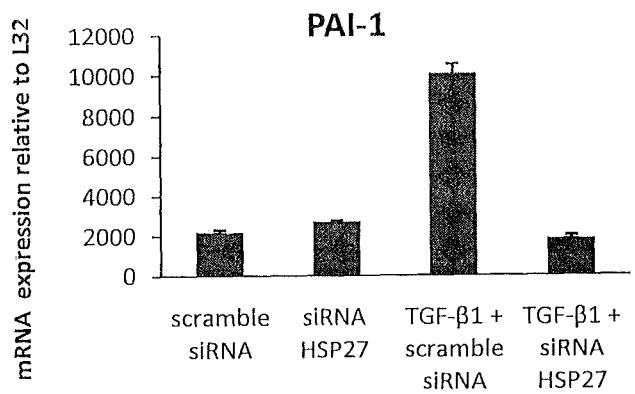
Figure 3D:
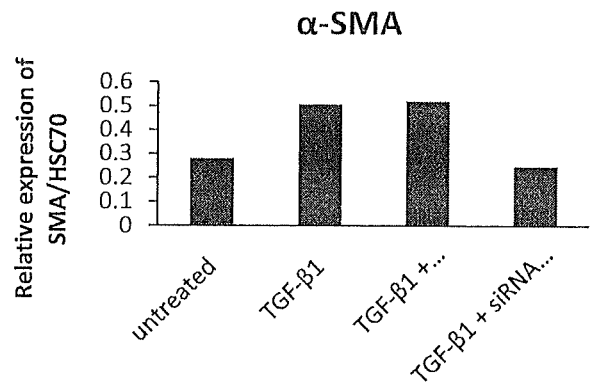
FIGS. 3D-F show protein levels for α-SMA, E-cadherin and PAI-1, respectively, after treatment with a scrambled siRNA control, anti-HSP27 siRNA, scrambled siRNA control plus rTGF-β1, or anti-HSP27 siRNA plus rTGF-β1 ((10 ng/ml, 48 h)). Bars, SD (n=4).
Figure 3E:
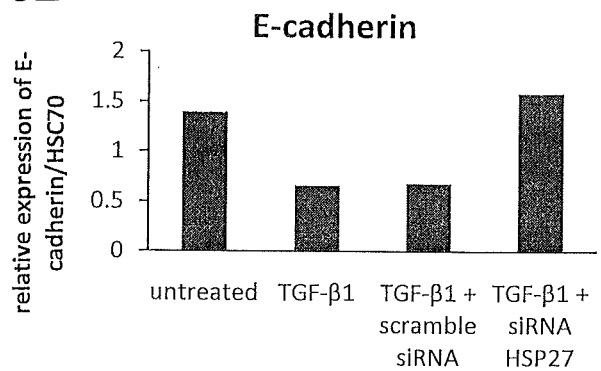
Figure 3F:
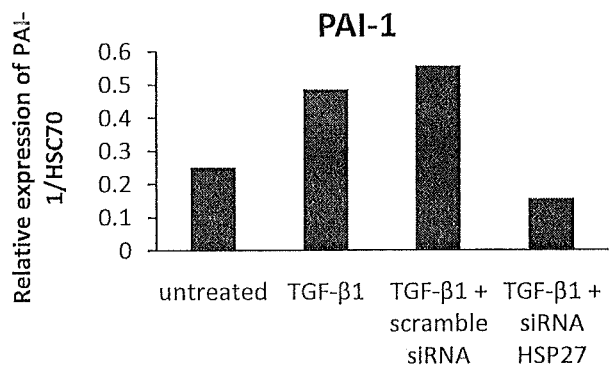
Figure 3G:
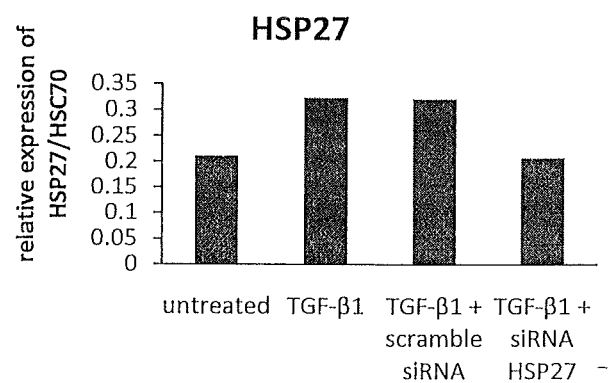
FIG. 3G shows relative expression of HSP27 (based on HSC70 expression) after treatment with TGF-β1 alone and with si-RNA targeting hsp27 or a scrambled control.

To further demonstrate the inhibitory role of HSP27 depletion in this EMT process, we performed a scratch test on mesothelial Met-5A cells in vitro to analyze the acquisition of a migration capacity after treatment with rTGF-β1. Cells treated with rTGF-β1 alone and with rTGF-β1/scramble siRNA had a strong migration capacity and the wound was totally recovered by cells within 48 hours. In contrast, untreated cells or HSP27 siRNA cells treated with rTGF-β1 presented a much weaker migration and, by 48 h, the wound was still largely unrecovered. Therefore, HSP27 inhibition blocked this all well known features of EMT induced by TGF-β1 in cultured cells. This corresponded to HSP27 expression levels (FIG. 3G).

Next, we tested the second generation antisense oligonucleotide OGX-427. Primary mesothelial cells treated with an antisense oligonucleotide (ASO) control were, as expected, able to spontaneous go through EMT with the successive passages in vitro as demonstrated by the increase in α-SMA and HSP27 expression. In sharp contrast, in the cells receiving OGX427, the increased expression of HSP27 and α-SMA observed with the cell passages was blocked. Moreover, cells receiving OGX427 kept their mesothelial phenotypic shape in contrast to control ASO treated cells, further proving the EMT blockage induced by OGX-427. A similar inhibitory effect for OGX-427 was observed in human mesothelial MET-5A cells in which EMT was induced by rTGF-β1.

Inhibition of HSP27 by OGX-427 Block Fibrosis In Vivo

To assess the role of HSP27 inhibition in the process of fibrogenesis in vivo, we administered OGX427 or its control ASO in the pleural cavity in our AdTGF-β1 induced pleural and subpleural fibrosis model in rats. The concentrations of ASO control and OGX-427 used were those previously described in studies of bladder cancer where the oligonucleotides were administered intra-vesically. (Matsui et al. *Mol Cancer Ther* 2009; 8:2402-11)

Figure 4A:
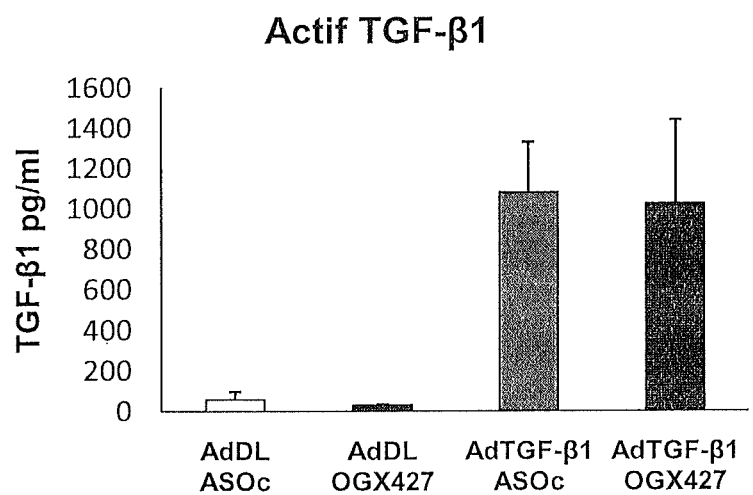
FIG. 4A shows ELISA measurement results of active TGF-β1 in PLF from rats that have received 6 days treatment by intra-pleural administration either an adenovirus control (AdDl) or an adenovirus encoding TGF-β1 (AdTGF-β1) together with an ASO control or OGX-427 (12 mg/kg). Bars, SD, n=9.
Figure 4B:
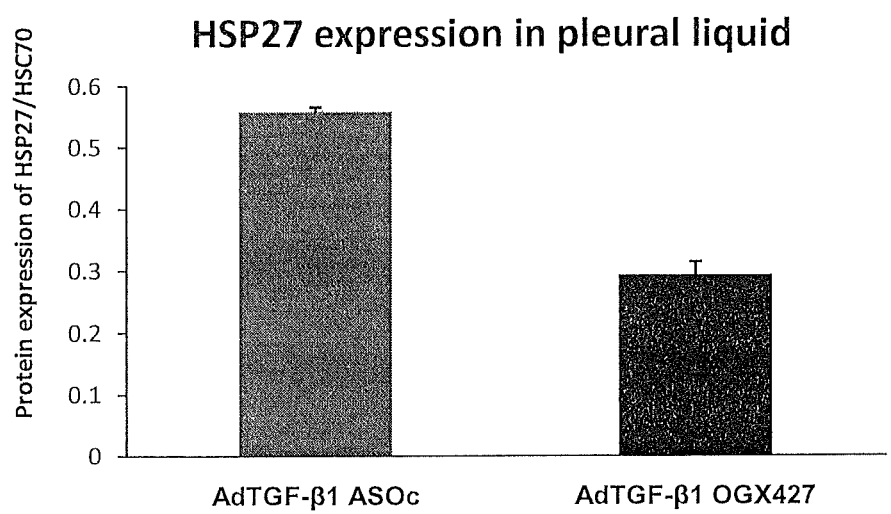
FIG. 4B compares Hsp27 protein expression in the pleural liquid of mice treated with AdTDF-β1 and a control antisense, with that in mice treated with AdTDF-β1 and OGX-427

After AdTGF-β1 or AdDL intrapleural administration, rats were daily treated with the ASO control or OGX427 during 6 days by intra pleural injection. We first confirmed by an ELISA technique that the content on TGF-β1 after AdTGF-β1 intrapleural administration was similar in the pleural lavage fluid (PLF) from all rats, those treated with OGX427 and those treated with a control ASO (FIG. 4A). A western blot on PLF confirmed that intra-pleural administration of OGX427 strongly blocked HSP27 expression. (FIG. 4B)

Figure 5A:
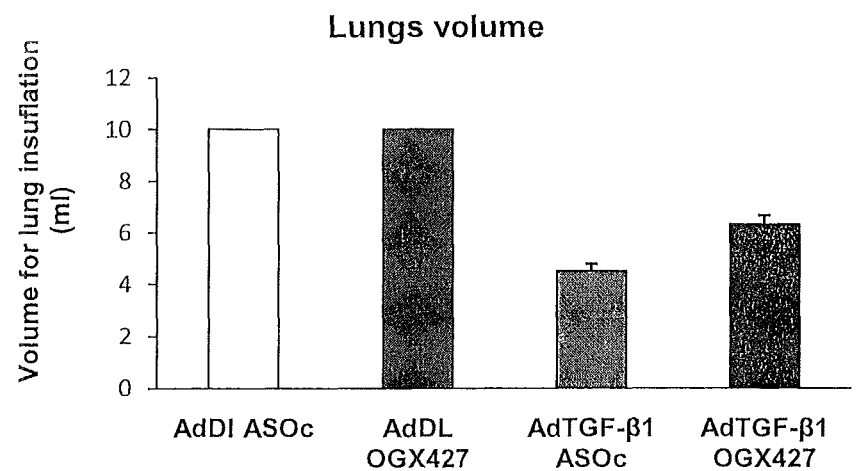
FIG. 5A shows the mean volume of RCL2 (fixation solution) necessary to insufflate the lungs in rats receiving either AdDL or AdTGF-β1 and/or OGX427 or an ASO control. 10 ml are necessary to insufflate a healthy lung. **p≤0.01, n=6.
Figure 5B:
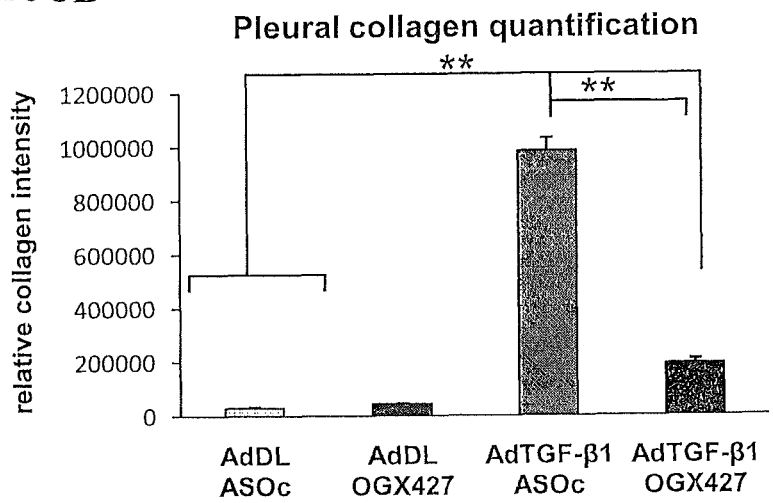
FIG. 5B shows quantification of pleural collagen as determined from microscopic images.

To determine lung activity, lung volumes were assessed by measuring the volume of RCL2 (fixation solution) that drained into the lungs after 10 min at a constant pressure of 20 cm H20. Compared to AdDL administered animals, AdTGF-β1 administration in ASO control rats induced a reduction in the lungs volume of 55%. Only a reduction of 35% was observed in OGX427 treated lungs (p<0.01 between ASO and OGX427. FIG. 5). This effect for the HSP27 inhibitor was only observed in the TGF-β1-exposed animals. In AdDL-administered animals, no difference in lung volumes was observed between ASO control- or OGX 427-treated animals (FIG. 5A). A histological evaluation of the lungs from rats treated with AdDL demonstrated that, consistent with other observation, those rats did not present any pleural/pulmonary fibrosis. Also, rats treated with AdTGF-β1 and receiving the control ASO had major pleural fibrosis with strong HSP27 and α-SMA overexpression. In contrast, rat lungs treated with AdTGF-β1 and receiving OGX427 had minor pleural fibrosis with a very significant decrease in HSP27 and α-SMA expression. FIG. 5B shows quantification of pleural coallagen based on microscopic images and demonstrates the substantial reduction in collagen in animals treated with OGX-427 when compared to those treated with AdTGF-β1 and a control antisense.

Figure 6:
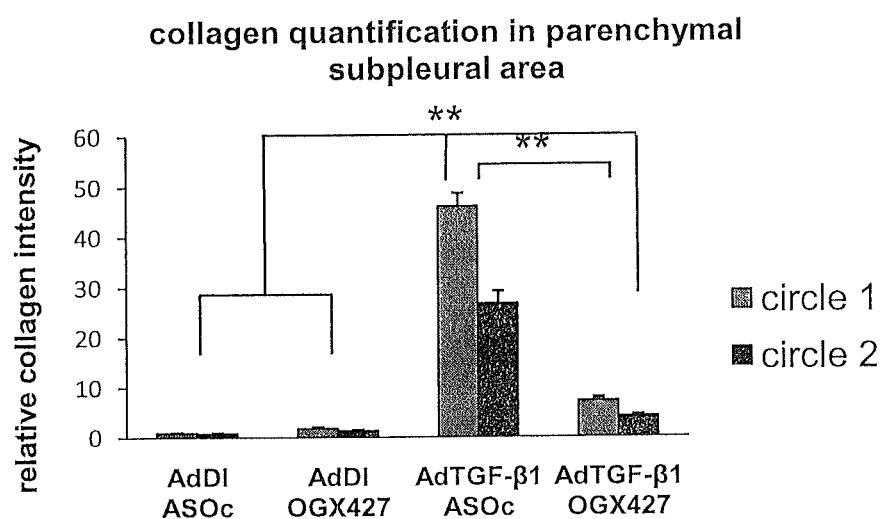
FIG. 6 shows quantification of collagen in parenchymal subpleural areas.

In a previous report where we co-administrated AdTGF-β1 together with AdLacZ, we demonstrated that during fibrosis development, mesothelial cells progressively migrated into the pulmonary parenchyma (DeCologne, 2007, supra). This AdTGFβ-1 induced migration of mesothelial cells expressing AdLacZ (blue cells) is not modified by the daily intrapleural administration of control ASO. In contrast, in OGX427 treated animals, the morphology of the cells did not change and no mesothelial cell migration within the subpleural parenchyma was observed. FIG. 6 shows quantification of collagen in parenchymal subpleural areas. We conclude that HSP27 inhibition by OGX-427 blocks mesothelial EMT process in vitro and in vivo thereby having a very significant repercussion in fibrosis development, and demonstrate that this reduces the amount of fibrosis in the pulmonary parenchyma.

All of the patents and publications referred to herein are incorporated herein by reference in their entirety, as if fully set forth herein.

From the foregoing, it can be seen that the present application provides advances over the art in the treatment of pulmonary fibrosis, including IPF. These advances include, without limitation those reflected in the following claims:

The invention claimed is:

1. A method for treatment of pleural or pulmonary fibrosis in a subject in need of such treatment comprising administering to the subject means for inhibiting heat shock protein 27 (HSP27).

2. The method of claim 1, wherein the pleural or pulmonary fibrosis is idiopathic pulmonary fibrosis (IPF).

3. The method of claim 1, wherein the pleural or pulmonary fibrosis is subpleural fibrosis, Usual Interstitial Pneumonia (UIP), or drug-induced lung fibrosis.

4. The method of claim 1, wherein the means for inhibiting HSP27 is administered by way of inhalation.

5. The method of claim 1, wherein the means for inhibiting HSP27 is administered by way of intra-pleural injection, intravenous injection, or intra-tracheal injection.

6. The method of claim 1, wherein the subject is human.

7. The method of claim 6, wherein the pleural or pulmonary fibrosis is idiopathic pulmonary fibrosis (IPF).

8. The method of claim 6, wherein the pleural or pulmonary fibrosis is subpleural fibrosis, Usual Interstitial Pneumonia (UIP), or drug-induced lung fibrosis.

* * * * *